(12) United States Patent
Fischer, Jr. et al.

(10) Patent No.: US 9,604,037 B2
(45) Date of Patent: Mar. 28, 2017

(54) CATHETER SYSTEMS AND METHODS USEFUL FOR CELL THERAPY

(71) Applicants: Cook Medical Technologies LLC, Bloomington, IN (US); Muffin Incorporated, West Lafayette, IN (US)

(72) Inventors: Frank J. Fischer, Jr., Bloomington, IN (US); James R. Randolph, Bedford, IN (US); Neal E. Fearnot, West Lafayette, IN (US); Jimmy L. Taylor, Jr., Spencer, IN (US); Gary Bradford Shirley, Bloomington, IN (US)

(73) Assignee: Muffin Incorporated, West Lafayette, IN (US)

( * ) Notice: Subject to any disclaimer, the term of this patent is extended or adjusted under 35 U.S.C. 154(b) by 475 days.

(21) Appl. No.: 13/910,693

(22) Filed: Jun. 5, 2013

(65) Prior Publication Data
US 2013/0338637 A1    Dec. 19, 2013

Related U.S. Application Data

(60) Provisional application No. 61/655,976, filed on Jun. 5, 2012.

(51) Int. Cl.
*A61M 31/00*     (2006.01)
*A61M 25/10*     (2013.01)
(Continued)

(52) U.S. Cl.
CPC .... *A61M 25/1011* (2013.01); *A61M 25/0026* (2013.01); *A61M 25/0041* (2013.01);
(Continued)

(58) Field of Classification Search
CPC .............. A61M 25/10; A61M 25/1018; A61M 25/10181; A61M 25/10182;
(Continued)

(56) References Cited

U.S. PATENT DOCUMENTS 4,848,344 A * 7/1989 Sos et al. ................... 606/194
6,293,920 B1 * 9/2001 Sweezer et al. ............ 604/6.14
(Continued)

OTHER PUBLICATIONS

Inter Search Rpt and Written Opinion—PCT/US2013/044287, 2013 NWM.

*Primary Examiner* — Edelmira Bosques
(74) *Attorney, Agent, or Firm* — Woodard, Emhardt, Moriarty, McNett & Henry LLP

(57) ABSTRACT

Described in one aspect is a multi-pressure monitoring system for cell or other therapy includes a first catheter having a first lumen for accepting a treatment device, a second lumen for inflating a balloon, a pressure sensor for monitoring fluid pressure within the first lumen, and a flow restrictor such as a hemostasis valve for limiting the exchange of fluids into and out of the first lumen while treatment devices are present or exchanged in the first lumen. Also disclosed is a method of using the first catheter with a first pressure monitor coupled to the first pressure sensor along with a second catheter attached to a second pressure sensor coupled to a second pressure monitor. The second catheter is positioned within the first lumen of the first catheter during treatment operations and the first and second pressure monitors are used to verify proper pressures throughout the procedure. Described also are novel methods, systems, and catheters for delivering flowable therapeutic substances, such as viable cellular preparations, to patients.

25 Claims, 9 Drawing Sheets

(51) Int. Cl.
*A61M 25/00* (2006.01)
*A61M 37/00* (2006.01)

(52) U.S. Cl.
CPC ........ *A61M 25/0068* (2013.01); *A61M 25/10* (2013.01); *A61M 37/0092* (2013.01); *A61M 25/007* (2013.01); *A61M 2025/0003* (2013.01); *A61M 2025/0004* (2013.01); *A61M 2025/0042* (2013.01); *A61M 2025/1015* (2013.01); *A61M 2025/1052* (2013.01); *A61M 2025/1061* (2013.01); *A61M 2025/1093* (2013.01)

(58) Field of Classification Search
CPC ...... A61M 25/10183; A61M 25/10184; A61M 25/10185; A61M 25/10186; A61M 25/10187; A61M 2025/0001; A61M 2025/0002; A61M 2025/0003; A61M 2025/0004; A61M 2025/1015; A61M 2025/1056; A61M 2025/1061; A61M 2025/1063

USPC .............. 604/96.01, 101.01, 101.03, 101.04, 604/101.05, 102.01, 102.02, 102.03, 604/164.01, 164.13, 167.01, 167.02, 604/167.03, 167.04, 171, 173, 500, 507, 604/508, 509

See application file for complete search history.

(56) References Cited

U.S. PATENT DOCUMENTS

| | | | |
|---|---|---|---|
| 7,686,781 B2 * | 3/2010 | Vinten-Johansen | 604/65 |
| 2002/0072647 A1 * | 6/2002 | Schock | A61B 5/0215 600/18 |
| 2005/0059930 A1 | 3/2005 | Garrison et al. | |
| 2005/0059931 A1 * | 3/2005 | Garrison et al. | 604/101.04 |
| 2011/0105960 A1 * | 5/2011 | Wallace | 601/2 |
| 2011/0270131 A1 * | 11/2011 | Snow | A61F 5/0056 600/587 |
| 2011/0319917 A1 | 12/2011 | Ferrera et al. | |

* cited by examiner

CATHETER SYSTEMS AND METHODS USEFUL FOR CELL THERAPY

This application claims the benefit of U.S. Provisional Patent Application No. 61/655,976, filed Jun. 5, 2012, which is hereby incorporated by reference.

BACKGROUND

This disclosure relates generally to medical devices and methods, and in certain of its aspects more particularly to catheter systems and associated methods which can be used for example in the delivery of cells to a patient.

In established and developing medical therapies, the administration of a therapeutic agent, such as a flowable medium containing cells, is often necessary. The therapeutic agent may be administered for example to treat an acute or chronic disease or condition. In these respects, the therapeutic agent may be introduced into tissue in any of a variety of regions in the patient. Oftentimes, the tissue is tissue of a solid organ such as the heart, kidney, liver, pancreas, spleen, intestine, skeletal muscle, bone, lung(s), reproductive organs, or brain.

One illustrative area of interest involves heart disease. Over 1.1 million people experience a myocardial infarction each year in the United States. These events occur because of oxygen deprivation due to a reduction in the oxygenated blood supplied to the myocardium (heart muscle tissue). Traditionally it was believed that damage to cardiomyocytes (heart muscle tissue cells) was permanent because of the absence of effective cardiac progenitor cells which are able to replace dead or damaged cardiomyocytes. Cardiomyocytes were thought to be terminally differentiated cells having lost their ability to naturally proliferate shortly after birth.

More recent work suggests that the human heart may in fact be capable of regenerating cardiomyocytes following injury to the myocardium. This has led to the proposal of various cell therapies seeking to strengthen or regenerate damaged myocardium to improve performance in the infarcted region. Treatment goals vary widely but generally fall into the categories of replacing dysfunctional, necrotic, or apoptotic cardiomyocytes with new functional cells (thereby decreasing infarct size and improving cardiac output), increasing the quality and quantity of contractile tissue, and promoting local angiogenesis (creation of new blood vessels). In order to achieve these goals, various therapies have been developed involving the delivery of different types of cells into the infarcted myocardium by various means with varying degrees of limited success depending on the circumstances and the method used.

One technique for delivering cells into the infarcted region of the myocardium is by retrograde perfusion from within a cardiac vein. With this technique, a vein opposite, or in the area of, an artery in the infarcted region is temporarily occluded using an expanding balloon catheter or similar device while a treatment agent containing the cells is introduced into the vein. The vein remains occluded during perfusion of the treatment agent to allow the treatment agent containing the cells the opportunity to be delivered into the capillaries of the tissue in the treatment region. The coronary sinus is a common entry point for this procedure because it is easily accessed from either the superior or inferior vena cava, and because venous pressures in the coronary sinus are significantly lower than arterial pressures making it more likely the treatment will succeed with less risk to the patient.

While delivery of cells to the heart as discussed above has received significant attention, many proposals and methods are also known for treating other diseased organs or tissue areas, such as those named above, with cells or other therapeutic agents.

There remain needs in this area for safe and effective devices, apparatuses, systems and methods for the delivery of cells and/or other substances into patient tissues.

SUMMARY

In various aspects, the embodiments disclosed herein are directed to catheters, systems and methods for delivering cells and/or other therapeutic substances to human or animal (veterinary) patients. Embodiments include catheter systems with multi-pressure monitoring capacity which can be used to facilitate enhanced monitoring and control of the delivery of the cells/therapeutic substance(s) to a patient. Embodiments also include unique catheter combinations for enhanced access and delivery to patient tissue regions, and catheters that can be used in such combinations.

Additional embodiment summaries can be understood from reference to the claims hereinafter, with it being understood that each claim is considered an embodiment disclosed.

Further, still additional embodiments will be apparent to those skilled in the art from the Detailed Description herein.

BRIEF DESCRIPTION OF THE DRAWINGS

FIG. 5 is a schematic diagram illustrating one exemplary use of the catheter shown in FIG. 4 or 4a.

DETAILED DESCRIPTION

Figure 1:
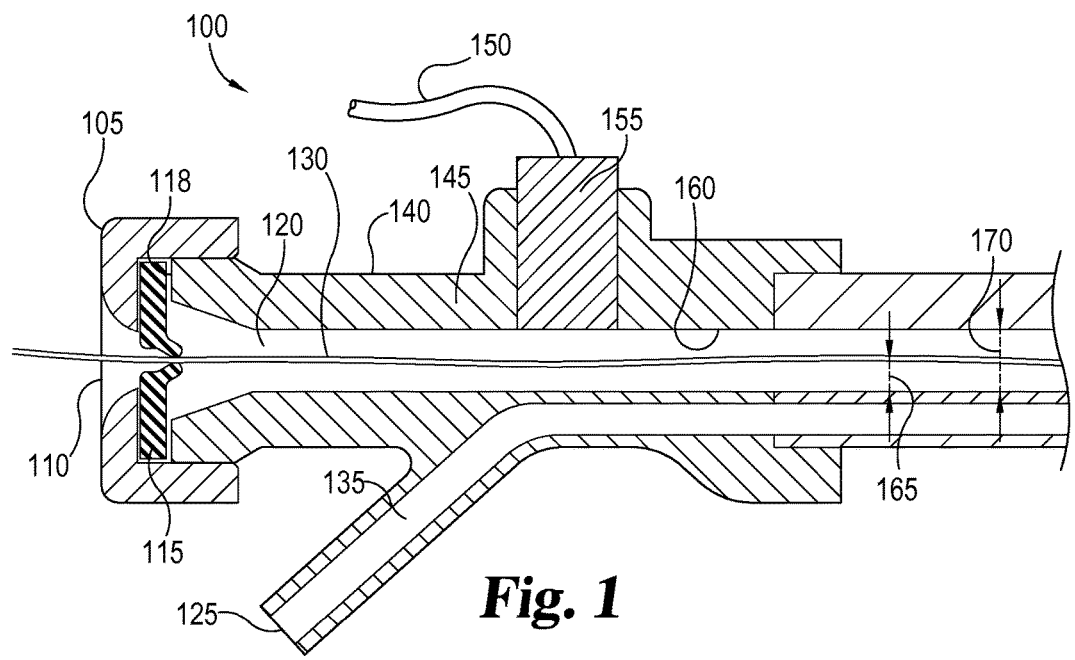
FIG. 1 is a longitudinal cross-sectional view of the proximal end of one example of a catheter for use in an infusion and pressure monitoring operation.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 2A:
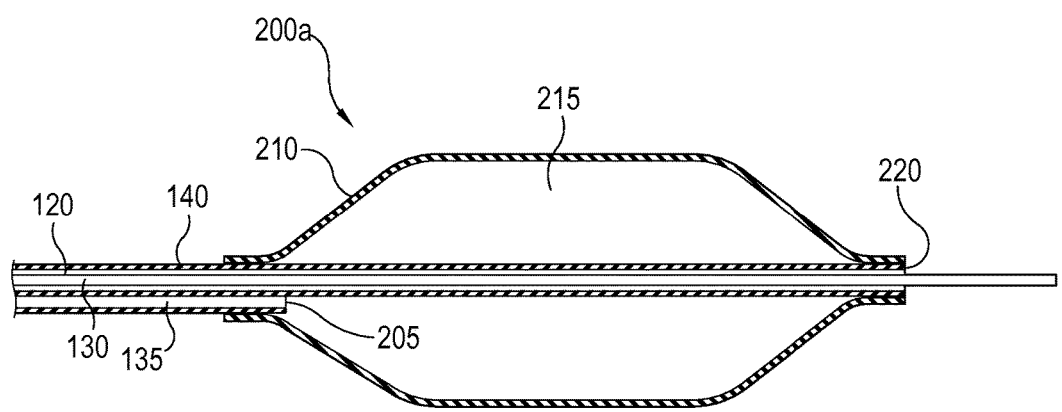
FIG. 2a is a longitudinal cross-sectional view of one example of the distal end of the catheter shown in FIG. 1.

FIG. 1 and FIG. 2a show a longitudinal cross-sectional view of one embodiment of a catheter which can be used in a liquid infusion and pressure monitoring system and method, e.g. for cell or other therapy to be administered to a human or animal (veterinary) patient. As shown, a proximal end of the catheter is shown in FIG. 1 at 100 and a distal end of the catheter is shown in FIG. 2a at 200a. The proximal end 100 has a first lumen which can receive a treatment device, a valve or other flow restriction device for example a resilient valve member operable to seal around the treatment device inserted through the lumen, attached to the proximal end of the catheter for restricting the movement of fluid into and out of the first lumen, a sensor operable to measure fluid pressure in the first lumen, and a second lumen extending into the catheter shaft for inflating an inflatable balloon.

First lumen 120 illustrated in FIG. 1 and FIG. 2a extends from a proximal tip 118 to a distal tip 220 of catheter shaft 140 and is configured so as to be capable of coaxially receiving a treatment device 130. First lumen 120 appears in FIG. 1 and FIG. 2a centered on the central axis of catheter shaft 140. However, other embodiments are also envisioned. In another embodiment, first lumen 120 is offset laterally from the longitudinal axis of catheter shaft 140. Also, first lumen 120 appears in FIG. 1 as a lumen having a circular cross-section. However, numerous embodiments of first lumen 120 are possible and FIG. 1 is meant to be illustrative rather than exclusive in nature. Other embodiments of first lumen 120 have half circle, ovular, partial circular, crescent, or hexagonal cross-sections. The cross-section of first lumen 120 need only be shaped to provide sufficient space for treatment device 130 such that treatment device 130 is not undesirably bent, kinked or twisted as it is advanced through first lumen 120 to the treatment region and clearance for transmission of fluid pressure (e.g. blood pressure) for pressure measurement as described herein.

Also, inside diameter 170 of first lumen 120 can vary widely. In one embodiment, inside diameter 170 of first lumen 120 is about 0.035 inches. However, inside diameter 170 can vary widely serving only as a limitation on the maximum outside diameter of treatment device 130. If treatment device 130 is too large, then the clearance 165 between treatment device 130 and inside wall 160 of first lumen 120 may be insufficient to allow effective liquid transfer between the treatment region in the area around distal tip 220 and pressure sensor 155 so that pressure sensor 155 can effectively detects pressure changes occurring in the treatment region. Clearance 165 can vary depending on the application and the circumstances specific to the use of the catheter including the type of fluids being engaged and the working pressures within the treatment area. For example, in one embodiment, treatment device 130 is a second catheter. When such is the case, the second catheter can be used for subselective catheterization of a tissue region to receive delivery of the therapeutic substance, preferably a cellular preparation. For example, Cantata™ catheters commercially available from Cook Medical, Bloomington, Ind., USA or from other commercial sources, or other subselective catheters as described herein, can be used for such subselective catheterizations. In certain embodiments, the subselective catheter as used herein will have a catheter shaft with a French size of about 3 French or less (outer diameter of about 1 mm or less). It has been discovered that subselective and precise catheterization of relatively small vascular vessels such as those which occur in venous beds, and delivery of cells through the subselective catheter, can lead to dramatic improvements in the delivery and retention of the cells in the associated tissue volume, for example as compared to simply forcing the cells under pressure out of the distal end of the larger outer catheter. In certain embodiments, the second, subselective catheter can be a so-called microcatheter, and can have a shaft size of 3 French or less (or an outer diameter of about 1 mm or less), and in some forms of about 1 French to 2 French (or an outer diameter of about 0.3 mm to about 0.7 mm). Further, in other embodiments, treatment device 130 is or can include a guidewire. Illustratively, in some embodiments the treatment device can be a combination of a subselective catheter and a guidewire extending through a lumen of the subselective catheter (which can help to stiffen the subselective catheter during advancement). For example, where the subselective catheter has an outer diameter of about 0.5 mm, the guidewire may have a smaller outside diameter, for example about 0.35 mm. Other sizes, however, may be used. Where the subselective catheter is to be used to deliver a flowable cellular and/or other therapeutic preparation, and the inserted guidewire is in the intended delivery lumen for the preparation, the guidewire may be removed prior to the delivery.

Figure 2B:
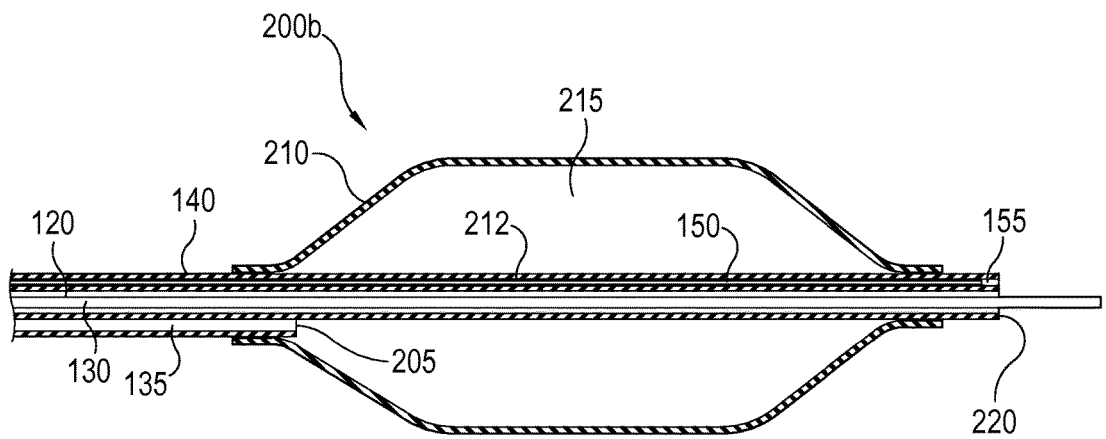
FIG. 2b is a longitudinal cross-sectional view of a second embodiment of the distal end of the catheter shown in FIG. 1.

Other treatment devices 130 are envisioned as well. In some situations, treatment device 130 can be a sensing, scanning, ultrasound, or other active or passive probing device performing angiography or other complex two-dimensional, or three-dimensional mapping procedures within the treatment region. In still other treatment scenarios, treatment device 130 can include a plurality of instruments such as first a guidewire in combination with a catheter or other treatment device received thereover, e.g. a catheter similar to that illustrated in FIG. 1 and FIG. 2a or FIG. 2b. Of course numerous other uses of the catheter illustrated in FIG. 1 and FIG. 2a or FIG. 2b are also envisioned as will be appreciated by one of ordinary skill in the art.

As can be seen in the embodiment illustrated in FIG. 1 and FIG. 2a, first lumen 120 opens at first proximal port 110 and extends from proximal tip 118 to a distal opening or port 220 at the catheter distal tip allowing treatment device 130 to pass through catheter shaft 140 along its longitudinal axis. Distal port 220 is positionable in the treatment region so as to be exposed to fluid (e.g. blood) pressure there occurring, which pressure can be transmitted proximally up the associated lumen 120. Various other embodiments are also envisioned. In another embodiment, treatment device 130 exits catheter shaft 140 through a lateral port some distance proximal to distal port 220 exiting through catheter shaft wall 145 rather than distal port 220. In this arrangement, distal port 220 is blocked or not present. Likewise in another embodiment, first port 110 and flow restrictor 115 are positioned distal to proximal tip 118 laterally along the outside of catheter shaft wall 145. In this arrangement, first lumen 120 deflects at an angle relative to the longitudinal axis of catheter shaft 140 to maintain fluid communication with first port 110 and flow restrictor 115 whose central axis is not parallel to the longitudinal axis of catheter shaft 140.

Figure 2C:
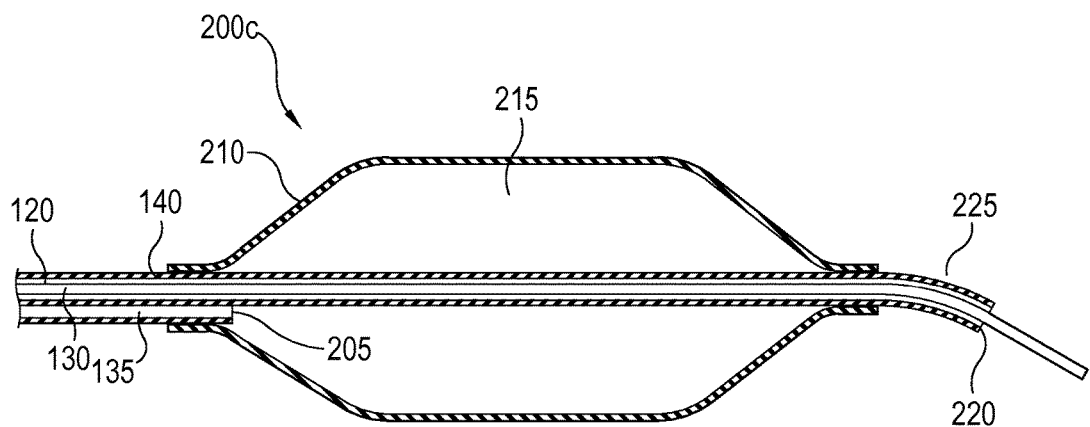
FIG. 2c is a longitudinal cross-sectional view of a third embodiment of the distal end of the catheter shown in FIG. 1.

In yet another embodiment, both first port 110 enters from a lateral position distal to proximal tip 118, and distal tip 220 is blocked with at least one exit port some distance proximal to the blockage at distal tip 200. These various embodiments may be advantageous depending on the treatment scenario, the treatment region, and the specific treatment agent involved. In another aspect, distal tip 220 is shown in FIG. 2c with a set curve 225 for easier navigation through the various blood vessels and particularly through the heart vessels themselves. By adding a set curve 225, such as an angiographic curve known in the art, to distal tip 220, the navigability of the catheter can be improved. The angle of curve 225 can be any suitable angle relative to the longitudinal axis of catheter shaft 140, for example an angle in the range of about 3 degrees to about 90 degrees. In some embodiments, the angle of curve 225 will be between 45 and 90 degrees relative to the longitudinal axis of catheter shaft 140, while in others, an angle between 0 and 45 degrees may be preferable. Set curve 225, or any other set curve identified herein, can for example be provided by a maleable wire that may be manually bent to a desired curve, e.g. by a health care provider immediately prior to use, or can be a resilient memory set curve provided by a polymeric material from which the curved shaft region is constructed and/or by a resilient wire or other element incorporated or otherwise associated with the catheter shaft.

Also shown in FIG. 1 is a first port 110 positioned at the proximal tip 118 of catheter shaft 140 and that is operable to provide access to first lumen 120. First port 110 opens into first lumen 120 and is therefore in fluid communication with first lumen 120. Fluid flow into and out of first lumen 120 and first port 110 is restricted by flow restrictor 115, such as a resilient valve member, mounted across first port 110 at the proximal end of first lumen 120. Flow restrictor 115 can prevent or substantially provide the escape of fluid from first lumen 120 through first port 110 even after treatment device 130 has been received into first lumen 120 and projects out of first port 110. Flow restrictor 115 can function to seal first port 110 before, during, and after the introduction of treatment device 130. One embodiment of flow restrictor 115 is a hemostasis valve as known to one of ordinary skill in the art. In the embodiment illustrated in FIG. 1 and FIG. 2a, first port 110 and flow restrictor 115 are arranged and aligned concentrically along a longitudinal axis of catheter shaft 140 to minimize mechanical interference when inserting treatment device 130 into the interior of first lumen 120. However, other configurations are possible. For example, as previously mentioned, in another embodiment of proximal end 100, first port 110 and flow restrictor 115 are angled away from the longitudinal axis of catheter shaft 140 requiring a treatment device 130 entering first lumen 120 through first port 110 and flow restrictor 115 to then bend at an angle before continuing through the remainder of lumen 120. In another embodiment, first port 110 and flow restrictor 115 are in separate locations along first lumen 120 such that flow restrictor 115 maintains hemostasis elsewhere within first lumen 120 while first port 110 provides entry into first lumen 120 from a separate location along first lumen 120 within catheter shaft 140.

As shown in FIG. 1, flow restrictor 115 is attached to catheter shaft 140 by an attachment collar 105. In the embodiment illustrated in FIG. 1, attachment collar 105 is coupled to catheter shaft wall 145 in order to securely maintain flow restrictor 115 in place so that pressurized fluid within first lumen 120 during the operation with the catheter cannot significantly escape around flow restrictor 115 between attachment collar 105 and flow restrictor 115, or between attachment collar 105 and catheter shaft wall 145. In one embodiment, attachment collar 105 and flow restrictor 115 are manufactured along with catheter shaft 140 and attachment collar 105 is therefore not a piece designed to be separated from catheter shaft wall 145. In another embodiment, attachment collar 105 is manufactured as a piece separate from catheter shaft wall 145, but is permanently attached to catheter shaft wall 145 by any of various means including thermal bonding, adhesive bonding, bonding by chemical reaction, or other non-detachable permanent means. In yet another embodiment, attachment collar 105 is manufactured as a piece separate from catheter shaft wall 145 that can also be removed and replaced. In this embodiment, attachment collar 105 is coupled by any one of various nondestructive detachable means such as by a threaded connector, snap fit, interference fit, friction fit, or other removable means thereby allowing flow restrictor 115 to be removed from proximal tip 118 of catheter shaft 140.

Continuing with other aspects shown in FIG. 1, sensor 155 is operable to measure fluid pressure in first lumen 120. Sensor 155 is mounted in catheter shaft 140 within or through catheter shaft wall 145 such that pressures in first lumen 120 are communicated to pressure sensitive areas of sensor 155. Various embodiments of sensor 155 are envisioned including transducers, solid-state pressure sensors, or sensors employing mechanical components and the like. Any device capable of determining, indicating, and relaying fluid pressure that is small enough to be positioned in catheter shaft 140 could be used. In the embodiment shown in FIG. 1, a sensor 155 is manufactured as a separate electronic component and permanently fixed within catheter shaft wall 145 by adhesive bonding, chemical bonding, thermal bonding, or other fixation means. In another embodiment, sensor 155 is manufactured as a separate electronic component and created with lugs, threads, notches, or other attachment means that allow it to be removable from catheter shaft wall 145 such as by a threaded connection, snap fit, interference fit, friction fit, or other removable means. In yet another embodiment, sensor 155 is a mechanically actuated diaphragm or other mechanical device capable of communicating changes in fluid pressure within first lumen 120 to an analog dial or display. In this embodiment, the mechanically actuated diaphragm is threaded into catheter shaft wall 145 and is removable by unscrewing the device. In those embodiments where sensor 155 generates electronic signals indicating changes in pressure within first lumen 120, the collected data is transmitted to an external device for analysis and display through transmission device 150 illustrated in FIG. 1 as a wire. However, in another embodiment, sensor 155 includes a miniature transmitter and the transmission device 150 illustrated in FIG. 1 is an antenna coupled to a transmitter (not shown) coupled to sensor 150 which transmits to a wireless data collection device. In another embodiment, sensor 155 is a mechanical pressure monitoring device with internal components operable to measure fluid pressure within first lumen 120. Such a device indicates fluid pressure in first lumen 120 using an external indicator such as a dial, gauge, meter, measuring post, and the like extending through catheter shaft wall 145. In this embodiment of sensor 155 and electronic transmission device 150 as depicted in FIG. 1 is not used. Rather than collecting and displaying pressure data on a digital graphic display, the information is displayed on an analog device and recorded manually by an operator.

Another mode of determining fluid pressure is illustrated at 200b in FIG. 2b. In FIG. 2b, sensor 155 is positioned at distal tip 220 with transmission device 150 coupled to sensor 155 and passing through a transmission lumen 212 to proximal end 100 of catheter shaft 140. Transmission lumen 212 extends longitudinally through catheter shaft 140 and has an opening in the vicinity of proximal end 100 (not shown) to allow transmission device 150 to exit catheter shaft 140 to facilitate connection to a data collection and reporting device. Sensor 155 is positioned at distal tip 220 such that it is operative to measure fluid pressure in the treatment area around distal tip 220 and communicate the pressure data via transmission device 150 (for example, a wire) to a data collection and analysis device. This alternate positioning facilitates the insertion of larger diameter treatment devices 130 into first lumen 120 without concern for inadequate communication of fluid pressure through first lumen 120 to pressure sensor 155 because of reduced clearance 165. It also may eliminate false pressure readings caused by blockages or obstructions which may have formed between treatment device 130 and inside surface 160. Also, in certain forms, placing pressure sensor 155 at distal tip 220 allows for a reduction in the overall outside diameter of catheter shaft 140 making it easier to maneuver the catheter through the various blood vessels and organs.

In another aspect, FIG. 1 also illustrates a second port 125 which is operable to allow access to a second lumen 135. Second lumen 135 extends through catheter shaft 140 terminating at inflation outlet 205 which is within inner void 215 of an inflation balloon 210 (see FIG. 2a). In this embodiment second lumen 135 operates as a balloon inflation lumen for inflatable balloon 210 shown inflated in FIG. 2a. In operation, second port 125 is connected to an inflation source which pushes an inflation medium such as a liquid or other suitable fluid into second lumen 135 through second port 125 and into inner void 215, thereby inflating inflatable balloon 210. Second lumen 135 appears in FIG. 1 and FIGS. 2a-2c as round and positioned along first lumen 120 parallel to the longitudinal axis of catheter shaft 140. However, in another embodiment, second lumen 135 and first lumen 120 are concentric with first lumen 120 and second lumen 135 positioned one inside the other and extending through catheter shaft 140. As with the first lumen 120 discussed above, second lumen 135 need not be round and may be embodied in various other cross sectional shapes such as crescents, half circles, and the like. Also, FIG. 1 shows second port 125 entering catheter shaft 140 from a lateral position deflected at an angle from the longitudinal axis of catheter shaft 140. Numerous other possible arrangements are also envisioned. For example, in another embodiment, second port 125 enters catheter shaft 140 from the proximal end in a manner similar to first port 110 from an opening adjacent to first port 110 such that both first port 110 and second port 125 open adjacent to one another at proximal tip 118 of catheter shaft 140. In another alternative embodiment, second port 125 enters catheter shaft 140 from a lateral opening entering at right angles to the longitudinal axis of catheter shaft 140.

Various modes of construction are possible for the catheter shown in FIG. 1 and FIGS. 2a-2c. For example, FIG. 1 shows catheter shaft 140 as being constructed of multiple materials. However this is not the only mode of construction envisioned. In one embodiment, proximal end 100 is constructed of a polycarbonate, metal, or similarly rigid material strong enough to firmly maintain sensor 155 in catheter wall 145 while also maintaining openings for first port 110, second port 125, and proper mounting for flow restrictor 115 at the proximal end of the catheter. In this embodiment, a much more flexible material is used for the remainder of catheter shaft 140 to the distal end 200a which extends into the patient's body, through the various blood vessels, organs and other tissue structures, and into a treatment site. The proximal end of distal end 200a is attached to the distal end of proximal end 100 by thermal bonding, adhesive bonding, bonding by chemical reaction, or other non-detachable means as shown in FIG. 1. Other embodiments may be desirable, such as an embodiment with a detachable coupling using a threaded or snap fit coupler at the junction between proximal end 100 and distal end 200a which allows proximal end 100 and distal end 200a to be nondestructively detachable rather than permanently coupled together. In another embodiment, catheter shaft 140 is manufactured of a single substance meaning proximal end 100 and distal end 200a are manufactured of the same material as a single piece. On the other hand, another embodiment of catheter shaft 140 is manufactured from several substances which progress from very rigid toward proximal end 100 to provide strength and durability to very pliable and flexible at the distal end 200a and 200b to make it easier to navigate catheter shaft 140 through the various structures to a treatment area. In yet another embodiment, catheter shaft 140 is manufactured in a single piece from a biocompatible polymer embedded with radiopaque marking rings, dots, lines, or other indices at various points along catheter shaft 140, including distal tip 220. In yet another embodiment, catheter shaft 140 is constructed using a radiopaque filler, such as barium sulfate or other similarly reactive material, thereby making substantially all of catheter shaft 140 radiopaque. By introducing radiopaque compounds and markings, catheter shaft 140 becomes easier to observe under a fluoroscope making precise positioning within the body easier. Such markings may also make catheter shaft 140 more visible when used with other forms of visualization discussed in some detail below. In another embodiment, distal tip 220 has a magnetically reactive coil (not shown) which makes distal tip 220 visible under magnetic resonance imaging.

Figure 3:
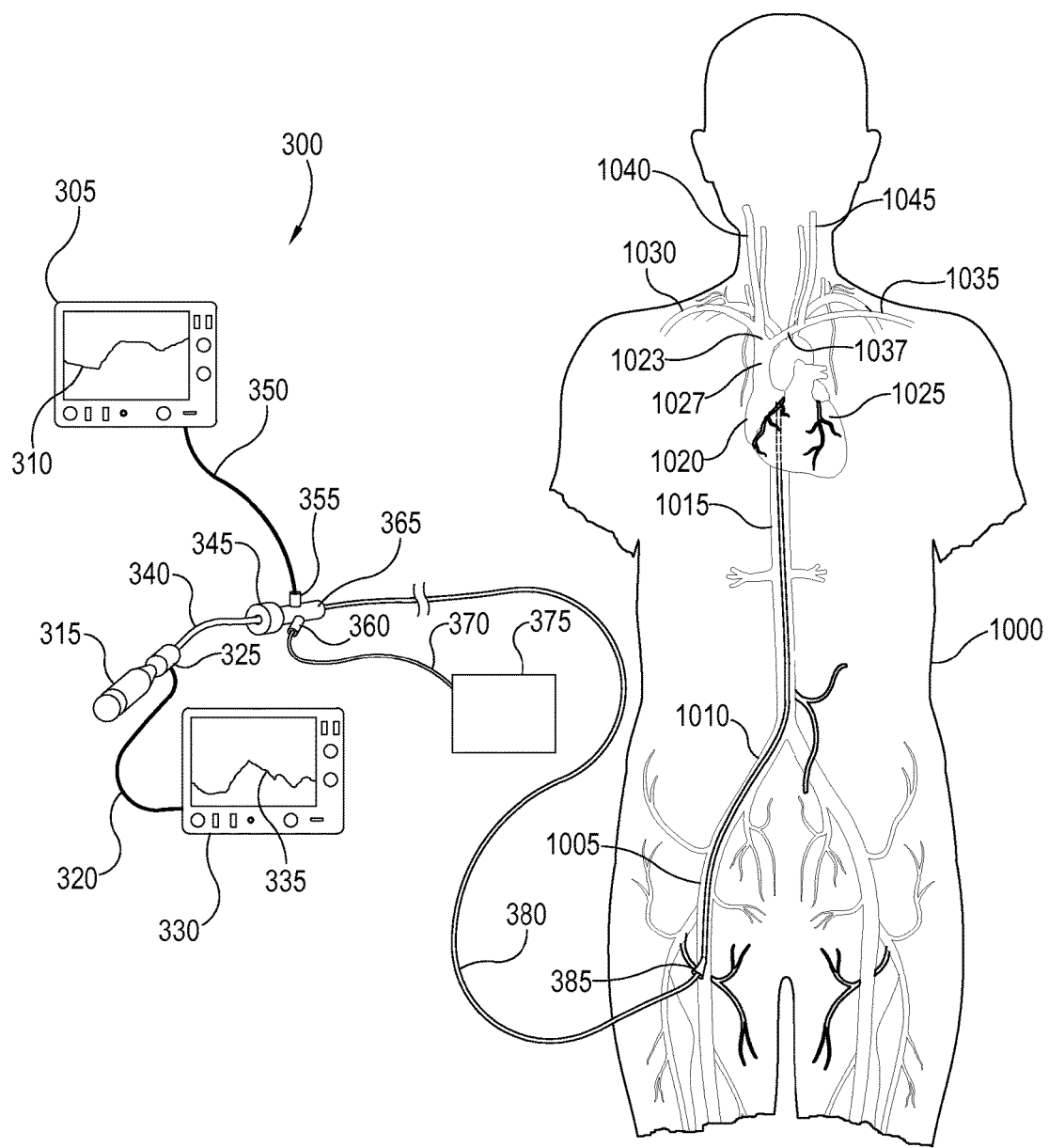
FIG. 3 is a schematic diagram illustrating one exemplary use of a catheter similar to those shown in FIG. 1 and FIGS. 2a-2c.

A catheter like the one shown in FIG. 1, FIG. 2a, or FIG. 2b is shown in FIG. 3 at 300 as part of a multi-point pressure monitoring system that may in some embodiments be used for therapy with delivered cells and/or other flowable therapeutic substance(s). In some embodiments, the cells and/or other substances may be delivered to a region of tissue in a patient. The perfusion (including in some modes retroperfusion into a vein(s)) of the cells or other therapeutic substances into tissue can be accomplished, for example, in a solid organ such as a heart, kidney, liver, pancreas, spleen, intestine, skeletal muscle, bone, lung(s), reproductive organ (s), or the brain, for example. Using the catheters or systems described herein, the flowable cellular or other therapeutic preparation can be introduced retrograde into a vein so as to create a venous back pressure that exceeds the venous forward pressure, causing flow to reverse in the vein. In some modes, this can in turn cause reverse flow in one or more capillaries, potentially also in associated ateriorles, and potentially also in associated arterial branches. The resulting pressure gradient(s) against the walls any one or all of these vessels can be sufficient to result in increased permeability of the wall and allow cells and/or other therapeutic substances to be delivered into adjacent tissues. It will be understood that other delivery, transit or tissue penetration modes for the cells or other therapeutic substances may also be used in other embodiments. As well, it will be understood that in any of these delivery techniques where retrograde venous introduction is applied, or in other retrograde venous delivery techniques described herein, the delivery system and methodology may include the use of a balloon catheter (e.g. another balloon catheter such as that illustrated in FIGS. 1-2c) or other means on the congruent arterial side to occlude arterial-side blood flow to enhance the transmural pressure gradient during retrograde perfusion delivery. Such arterial occlusion while retroperfusing the congruent venous segment can enhance vessel wall permeability and transmural penetration, migration and diffusion by the cells and/or other therapeutic substance. Still further, in addition to or as an alternative to the above modes for enhancing delivery of the cells and/or other therapeutic substance (and potentially penetration of the cells/substance into and/or through the vessel walls), at least one additional stress can be imparted to the vessel walls in the target treatment site, for example stress imparted by the application of ultrasound to the walls. In certain forms, such ultrasound is emitted from one or more ultrasound emitting elements mounted in a distal region of one or more of the catheters involved in the delivery procedure and positioned sufficiently near the target treatment site to impart the insonation-induced stress.

Turning now to one preferred illustrative use, FIG. 3 illustrates one embodiment of the system in operation as well as one location and path for positioning the distal end of a catheter of the type illustrated in FIG. 1, FIG. 2a, or FIG. 2b within the right atrium of the heart. Catheters other than those shown in FIG. 1, FIG. 2a, and FIG. 2b may be similarly positioned and used as well.

A first catheter 365 of a type similar to the one depicted in FIG. 1, FIG. 2a, or FIG. 2b is initially prepared for the procedure by coupling a first pressure monitor 305 to a first pressure sensor 355 by a first sensor wire 350. Initial setup continues by coupling a second pressure monitor 330 to a second pressure sensor 325 via a second sensor wire 320. Second pressure sensor 325 is coupled to a pressure increasing device 315 configured to deliver the treatment agent. One end of inflation tube 370 is coupled to second port 360 of first catheter 365 while the other end of inflation tube 370 is coupled to balloon inflation device 375 thus completing setup. Examples of various embodiments of balloon inflation device 375 include syringes, metered pumps, and various types of balloon inflation control devices used to monitor and control the pressure inside a catheter balloon. Examples of various embodiments of pressure increasing device 315 include a syringe, a metered pump, or any of various other types of pumps or infusers commonly used to push treatment agents through a catheter. Examples of various treatment agents which might be used in the procedure include blood or blood components, various pharmacological agents, infusion pellets, suspended cells, stem cells, microspheres, peptide growth factors, and the like.

One example of a treatment procedure using first catheter 365 establishing introducer sheath 385 in femoral vein 1005 in the thigh or groin area of patient 1000. Although FIG. 3 indicates introducer sheath 385 is inserted in the patient's right thigh, insertion in the left thigh or groin area is also envisioned and may be preferable depending on the individual patient's situation. A guidewire (not shown) is extends through introducer sheath 385 into femoral vein 1005. The guidewire preferably has a diameter between 0.014 and 0.018 inches and a flexible distal tip to make it easy to advance through the vasculature and into the vicinity of the selected target site, in this case the coronary sinus (not shown) attached to right atrium 1020 of the heart 1025. The guidewire is maneuvered into right atrium 1020 by guiding it into common iliac vein 1010, through inferior vena cava 1015, and into right atrium 1020 of heart 1025. The guidewire is then advanced into the coronary sinus (shown in more detail in FIG. 7) and into the vicinity of one or more coronary veins (not shown).

The proximal end of the guidewire projecting from introducer sheath 385 is positioned through the distal end of catheter shaft 380 finally exiting first port 345 of first catheter 365. With the guidewire extending through first catheter 365, catheter shaft 380 is maneuvered to the treatment site by gliding it over the guidewire through introducer sheath 385 into femoral vein 1005, along the path traversed by the guidewire up inferior vena cava 1015, into right atrium 1020 of the heart 1025 and into the coronary sinus. Balloon inflation device 375 is then engaged to inflate the balloon which is positioned near the distal end of first catheter 365 in the coronary sinus and/or the adjacent cardiac vein thereby holding catheter shaft 380 in position while also occluding the coronary sinus and/or cardiac vein. The guidewire is then withdrawn from first catheter 365 by retracting the guidewire proximally through first port 345. Throughout the withdrawal process, hemostasis can be maintained by a hemostasis valve or other flow restricting device (not shown) operatively coupled with first port 345 to keep any significant quantity of blood or other fluids from exiting first port 345 while the guidewire is being withdrawn from catheter shaft 380.

After the guidewire is withdrawn, second catheter 340 is inserted into first port 345 and advanced inside catheter shaft 380 through femoral vein 1005, into common iliac vein 1010, up inferior vena cava 1015, and into right atrium 1020 of the heart 1025. Second catheter 340 moves through catheter shaft 380 exiting its distal tip to enter the treatment area where it is then steered to the precise treatment location (see FIG. 7). As with the guidewire positioning and withdrawal steps, hemostasis may be maintained by a hemostasis valve or other similar flow restricting device operatively coupled to first port 345 such that no more than insignificant quantities of blood or other fluids escape catheter shaft 380 through first port 345 while the guidewire and second catheter 340 are being advanced and withdrawn. Throughout the procedure described here, standard medical procedures common to one of ordinary skill in the art can be followed to flush first catheter 365, second catheter 340 and other necessary equipment with a saline solution or similar fluid as necessary to minimize the opportunity for air pockets to be introduced into the patient's vasculature. As well, a guidewire or other guiding or stiffening member may be inserted into a lumen of second catheter 340 during advancement through first catheter 365. Such guidewire or other stiffening member may then optionally be withdrawn prior to administration of a cellular and/or other treatment agent as discussed below.

With second catheter 340 subselectively maneuvered into position within the treatment area, delivery of the treatment agent may commence. As illustrated in FIG. 3, second catheter 340 functions as a treatment catheter or treatment delivery device. Second catheter 340 is coupled to second pressure sensor 325. A fluid input device 315 then begins applying treatment agent under pressure into second catheter 340 thereby beginning the flow of treatment agent through a lumen of second catheter 340 (e.g. a lumen from which a guidewire or other stiffening member has been removed as discussed above) and into the treatment region. As treatment progresses, second pressure sensor 325 relays pressure data through second sensor wire 320 to second pressure monitor 330 which appears as second pressure data 335. Likewise first pressure sensor 355 supplies pressure data through first sensor wire 350 to first monitor 305 where it appears as first pressure data 310. Throughout the procedure, first pressure monitor 305 indicates the fluid pressure in the treatment region. Second pressure sensor 325, on the other hand, indicates fluid pressure of the treatment agent itself measured inside second catheter 340 as the treatment agent is being delivered into the treatment site. First pressure sensor 335 gauges fluid pressure and stress on the walls of the internal passages (e.g. blood vessels) in the treatment area while second pressure sensor 325 aids in gauging potential stress on the treatment agent itself (e.g. cells) or catheter structures caused by fluid pressure.

First pressure monitor 305 and second pressure monitor 330 appear in FIG. 3 as digital displays showing a historical graph of first pressure data 310 and second pressure data 335. However, other embodiments are also envisioned such as a mechanical gauge or other similar analog pressure indicator having no electronic components. In another embodiment, first pressure monitor 305 and second pressure monitor 330 only report the current pressure and have no ability to save past pressure data nor to indicate passed pressure data readings in a graphical form.

Figure 4:
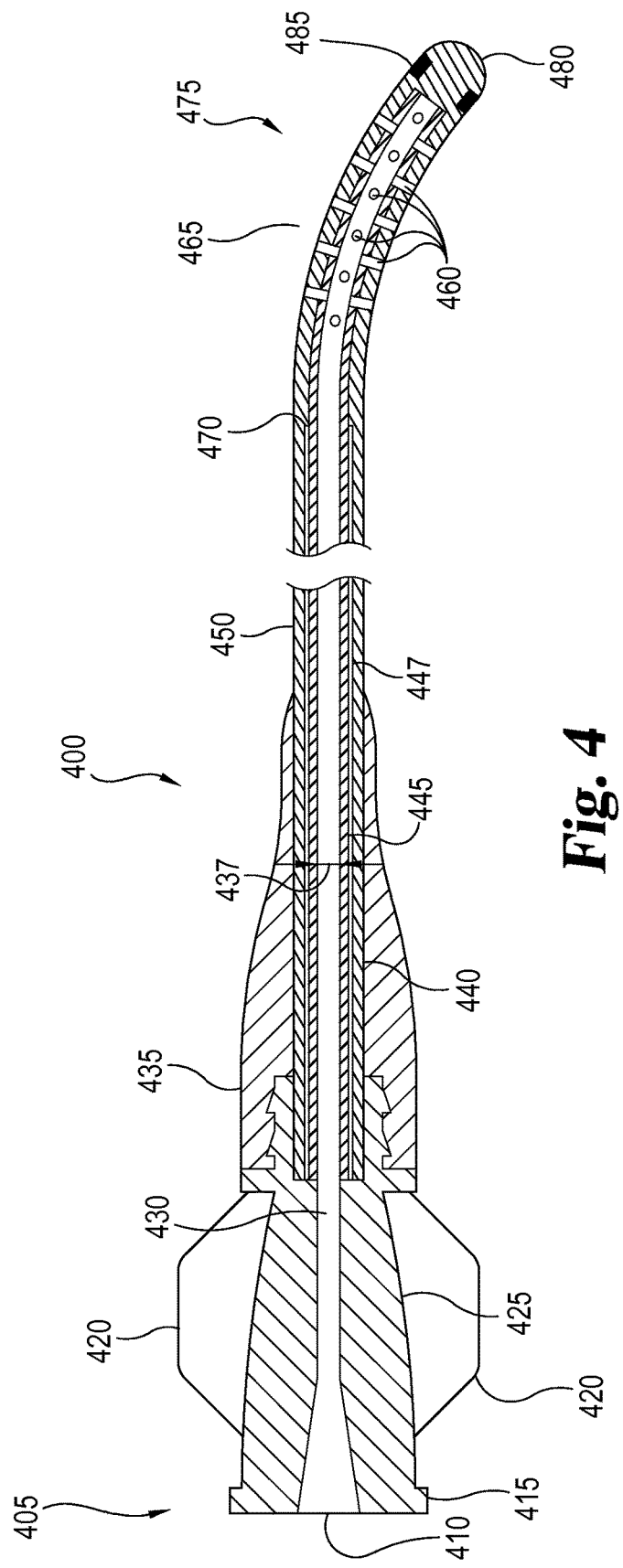
FIG. 4 is a longitudinal cross-sectional view of one example of a catheter for delivering a treatment agent, optionally for use subselectively with another catheter such as that shown in FIG. 1, FIG. 2a, and FIG. 2b.

Another embodiment of a catheter useful for delivering a treatment agent into a treatment region is shown at 400 in FIG. 4. The catheter at 400 has a proximal end 405 and a distal end 475 and a catheter shaft 450 extending between the two ends. Proximal end 405 has a connector or hub 425 for coupling to catheter shaft 450 which extends the length of the catheter terminating at distal tip 480. The proximal end of catheter shaft 450 is coupled to the distal end of connector 425 by any appropriate means such as thermal bonding, adhesive bonding, bonding by chemical reaction, or other non-detachable means as shown in FIG. 4. Other embodiments may be desirable, such as an embodiment with a detachable coupling using a threaded or snap fit coupler at the junction between connector 425 and catheter shaft 450 allowing them to be detachable rather than permanently coupled together.

Connector 425 has an attachment collar 415 and ergonomic grips 420 which make it easier to attach the catheter to various other devices. A flexible sleeve 435 surrounds the junction between connector 425 and catheter shaft 450 giving the joint additional strength and durability while also making it easier to grip the catheter when attaching it to other devices. Connector 425 has a central lumen port 410 at the proximal tip which provides access to a central lumen 430 having an inside diameter 437. In one embodiment, inside diameter 437 is 0.022 inches; however, other inside diameters are also envisioned depending on the treatment agent or other substance passing through central lumen 430 and the size constraints of the treatment area. In the embodiment illustrated at 400, central lumen 430 begins at proximal end 405 and continues along the central axis of catheter shaft 450 through the catheter and terminating at distal tip 480.

In the embodiment shown at 400, catheter shaft 450 is constructed of multiple concentric layers. Surrounding central lumen 430 is a liner 445 which separates substances passing through central lumen 430 from reinforcing material 447 and extends from the proximal end of catheter shaft 450 to distal tip 480. Reinforcing material 447 can provide extra strength (e.g. column strength) and/or durability to catheter shaft 450. Reinforcing material 447 extends from the proximal end of catheter shaft 450 to a termination region 470 some distance from distal tip 480. Surrounding reinforcing material 447 is flexible material 440 which makes up the outer shell of catheter shaft 450.

In one embodiment, reinforcing material 447 is a layer of woven or braided metal or other reinforcing material. In another embodiment, reinforcing material 447 does not surround central lumen 430 but rather is present as one or more separate reinforcing or stiffening members running through catheter shaft 450 between liner 445 and flexible material 440. In this embodiment, the separate reinforcing or stiffening member may be any sort of material providing increased rigidity such as one or more individual wires or rods made of plastic or metal. In another embodiment, flexible material 440 is composed of various materials with stronger, more rigid materials used toward the proximal end to better resist physical deformation of catheter shaft 450 while more pliable and flexible materials are used in more distal sections of catheter shaft 450 to make navigation through the vasculature less difficult.

At distal end 475, treatment catheter 400 has a set distal bend 465 which deflects distal tip 480 away from the longitudinal axis of catheter shaft 450 to aid in the navigation of treatment catheter 400 as it passes through the various structures on its way to a treatment region. Distal end 470 also has a plurality of side ports 460 which allow the treatment agent moving through central lumen 430 to diffuse through the sides of distal end 475 in various directions rather than exiting through distal tip 480. The embodiment shown at 400 indicates multiple ports 460. However no particular number or size of ports is intended by the illustration in FIG. 4. Distal end 475 could have one port, two ports, or any number of ports appropriate to the successful release of the treatment agent. As well, in addition to or as an alternative to side port(s) 460, catheter 400 may have a terminal distal port that directs fluids longitudinally out the very tip of catheter 400. Furthermore, FIG. 4 indicates ports 460 penetrate catheter shaft 450 at right angles to the longitudinal axis of central lumen 430. However, the angle of penetration indicated in FIG. 4 is illustrative only and various other angles are envisioned and may vary significantly depending on factors such as the treatment agent, the treatment region, the fluid pressure in central lumen 430 and the like. Also, the angle of distal bend 465 can be any suitable angle relative to the longitudinal axis of catheter shaft 450, for example an angle in the range of about 3 degrees to about 90 degrees. In some embodiments, the angle of bend 465 will be between 45 and 90 degrees relative to the longitudinal axis of catheter shaft 450, while in others, an angle between 0 and 45 degrees may be preferable.

Considering the construction of the catheter shown in FIG. 4, various modes are possible. For example, FIG. 4 shows catheter shaft 450 and connector 425 as being constructed of multiple materials and coupled together. However, in another embodiment, connector 425 and catheter shaft 450 are constructed of the same flexible material 440. In yet another embodiment, flexible material 440 is manufactured from a biocompatible polymer embedded with radiopaque marking indices appearing on the exterior surface of catheter shaft 450 as dots, lines, rings or other markings at various points, including distal tip 480 (see e.g. distal tip radiopaque marker 485). In yet another embodiment, catheter shaft 450 is constructed using radiopaque filler, such as barium sulfate, thereby making the entire shaft radiopaque. By introducing radiopaque compounds and markings, catheter shaft 450 is easier to observe under a fluoroscope simplifying the process of precise positioning within the body. In yet another embodiment, distal tip 480 can include a magnetically reactive coil to aid in visualization and positioning using magnetic resonance imaging. Such markings may also make catheter shaft 450 more visible when used with other forms of visualization discussed in some detail below.

Figure 4A:
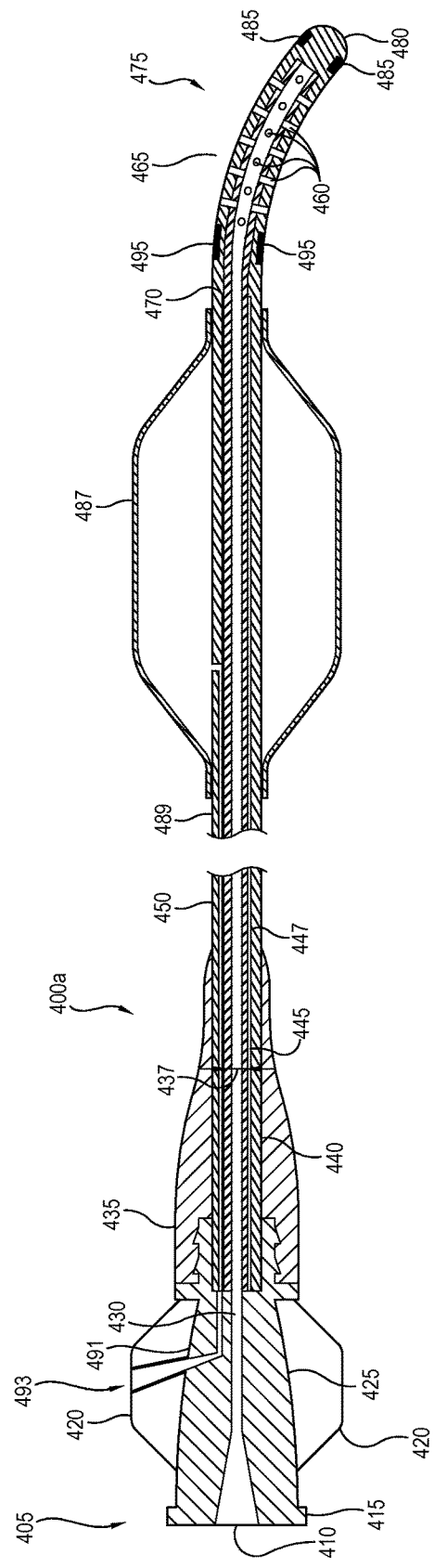
FIG. 4a is a longitudinal cross-sectional view of another catheter for delivery of a treatment agent, optionally for use subselectively with another catheter such as that shown in FIG. 1, FIG. 2a, and FIG. 2b.

FIG. 4a shows another catheter 400a which has similar features to catheter 400 discussed above, which are similarly numbered. In addition, catheter 400a includes an inflatable balloon 487 mounted on a distal region thereof, and an inflation lumen 489 fluidly communicating with and useful for passage of a fluid to inflate balloon 487. Inflation lumen 489 fluidly communicates with port lumen 491 and ultimately inflation port opening 493 of hub or connector 425. In certain modes catheter 400*a* can be used as a subselective catheter in conjunction with another catheter e.g. as described herein. Catheter 400*a* can be a microcatheter, for example having a catheter shaft with an outer diameter of about 0.018 inches or smaller. In one mode of use, balloon 487 can be inflated to occlude a vessel that has been subselectively catheterized (e.g. in conjunction with another, larger balloon catheter as described herein), and a viable cellular preparation and/or other therapeutic agent can be delivered through the delivery lumen 430 and out of ports 460. In other embodiments, in addition to or as an alternative to side ports 460, catheter 400*a* can have a distal tip opening providing a port for longitudinal delivery of the therapeutic preparation.

Figure 4B:
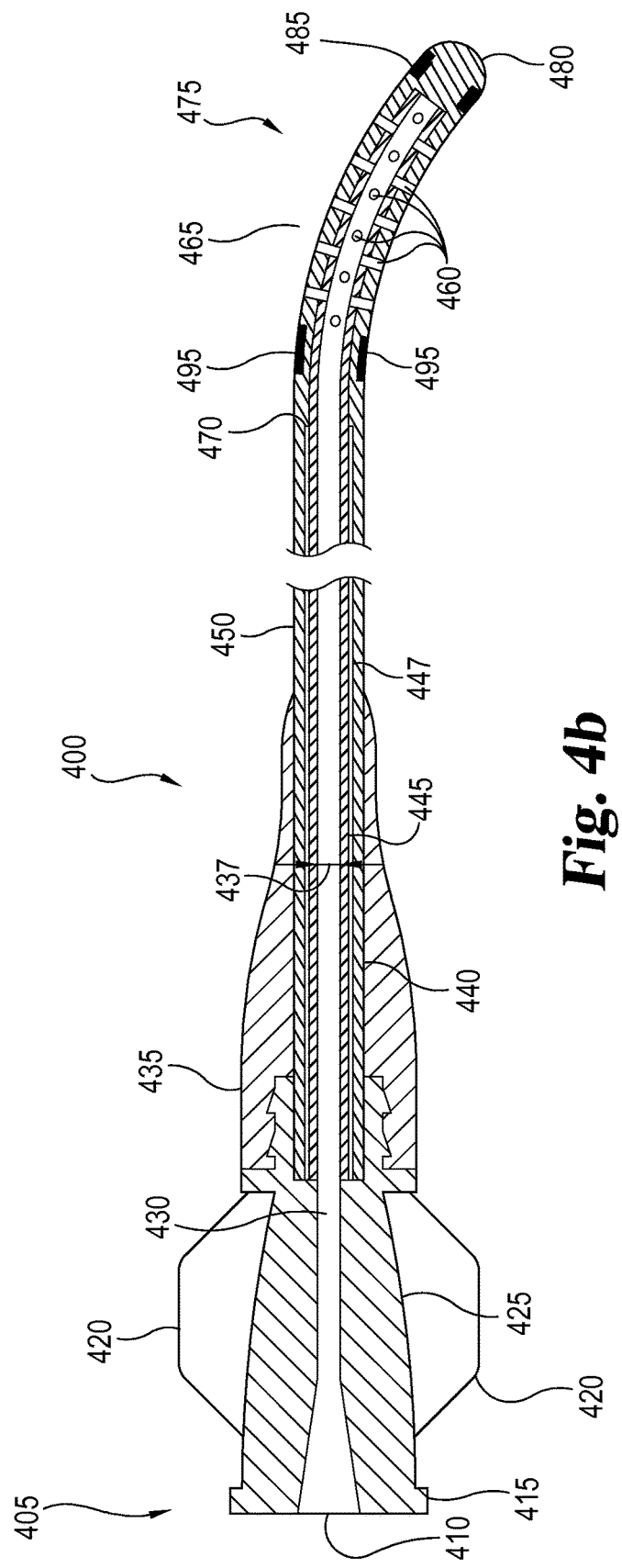
FIG. 4b is a longitudinal cross-sectional view of another catheter for delivery of a treatment agent, optionally for use subselectively with another catheter such as that shown in FIG. 1, FIG. 2a, and FIG. 2b.

FIG. 4*b* shows another catheter 400*b* which has similar features to catheter 400 discussed above, which are similarly numbered. In addition, catheter 400*b* includes an ultrasound emitting element 495 mounted on a distal region thereof. Element 495 is operable to emit ultrasound to the surrounding tissue region, and can for example be powered by a wire extending within a lumen wall of catheter 400*b* and/or within a dedicated lumen or shared lumen (e.g. lumen 430) of catheter 400*b*. Suitable piezoelectric ultrasound emitting devices are known and can be used herein. In certain modes of operation, ultrasound emitting element 495 can be operated before, during and/or after the delivery of a viable cellular and/or other therapeutic substance from ports 460, in order to enhance the delivery of the substance. In some modes of operation, the ultrasound emitted by element 495 can be effective to increase the penetration of the cells and/or other therapeutic substance through adjacent vessel (e.g. venous) walls. With reference now also back to FIG. 4*a*, catheter 400*a* may also include an ultrasound emitting element 495. As with catheter 400*a*, in other embodiments, in addition to or as an alternative to side ports 460, catheter 400*b* can have a distal tip opening providing a port for longitudinal delivery of the therapeutic preparation.

Figure 5:
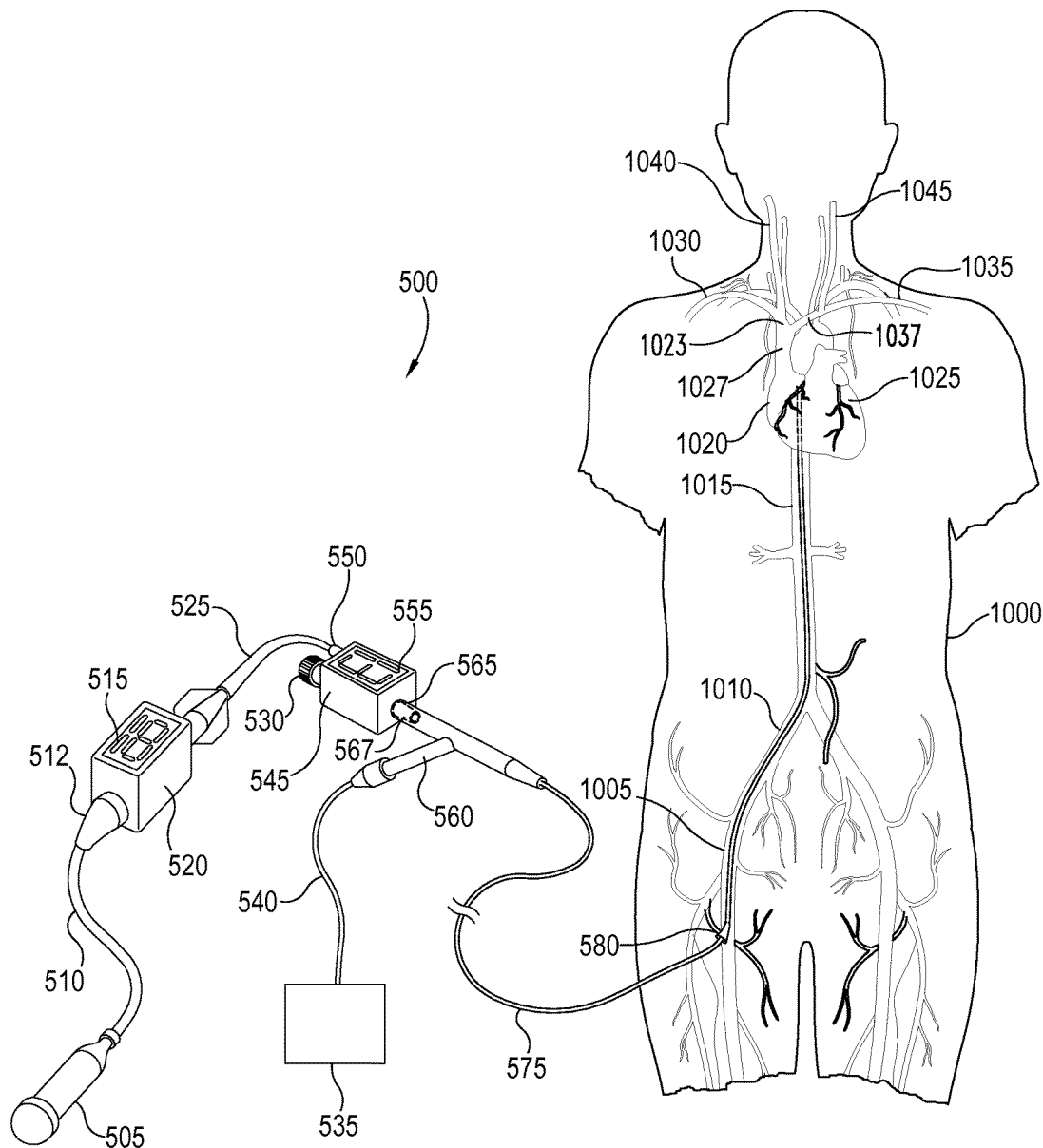

A multi-pressure monitoring system that may be used for cell therapy is shown in FIG. 5, which is similar to the system shown in FIG. 3. The system shown in FIG. 5 has a first catheter 570 having an inflatable occlusion balloon (not shown) at its distal end for occluding areas within the treatment region as required by the specific treatment regimen. Catheter 570 has a catheter shaft 575 and a first lumen port 565 at the proximal end for accessing a first lumen (not shown) which extends through catheter shaft 575 and exits at or near the distal end. First catheter 570 also has a balloon inflation port 560 which allows an inflation medium to pass through catheter shaft 575 inside a balloon inflation lumen (not shown) into the inflation void inside the occlusion balloon near the distal end of catheter shaft 575. Coupled to balloon inflation port 560 is a balloon inflation line 540 which carries the inflation medium from a balloon inflation device 535 through a balloon inflation port 560 into the balloon inflation lumen where it can be used to inflate the balloon. First pressure sensing device 545 is coupled to first lumen port 565 to measure the pressures inside the first lumen of catheter 570. First pressure sensing device 545 has an auxiliary inlet port 530 and a first treatment inlet port 550 and displays first pressure data 555 indicating the current pressure inside the treatment area. First pressure data 555 may be indicated by any indicator operable to communicate pressure to the user such as a liquid crystal display, arrangements of light emitting diodes, or by any of various analog indicators such as a needle in a gauge. A second catheter 525 enters first treatment inlet port 550, passes through first pressure sensing device 545, exits through first treatment outlet port 567, and enters the first lumen of first catheter 570 through first lumen port 565. Second catheter 525 passes through the first lumen of catheter shaft 575 exiting at or near the distal end of first catheter 570 into the treatment area. Second catheter 525 maintains a sealing relationship with first treatment inlet port 550 so that throughout the treatment procedure, no significant quantities of blood or other fluids can exit from first treatment inlet port 550 before, during and after second catheter 525 is inserted into first treatment inlet port 550. A second pressure sensing device 520 is coupled to second catheter 525 to measure the fluid pressure inside second catheter 525. Second pressure sensing device 520 displays second pressure data 515 indicating the current pressure inside second catheter 525 as treatment progresses. As with first pressure data 555, second pressure data 515 may be indicated by any sort of indicator such as a liquid crystal display, a light emitting diode display, or by any of various analog indicators such as a needle in a gauge. Treatment line 510 is coupled to a second treatment inlet port 512 allowing the treatment agent passing from pressure increasing device 505 to move through treatment line 510, second treatment inlet port 512, second pressure sensing device 520, second catheter 525, and into the treatment region. Suitable digital pressure monitors for use for first pressure sensing device 545 and second pressure sensing device 520 are commercially available from Mirador Biomedical (Seattle, Wash.) under the brand name Compass™.

In operation, one embodiment of the system shown in FIG. 5 can be provided in initially disassembled condition such that catheter 570, balloon inflation line 540, first pressure sensing device 545, second catheter 525, second pressure sensing device 520, treatment line 510, and pressure increasing device 505 are not coupled together. However, in other embodiments, some or all of these components may already be coupled together using either nondestructively detachable or nondetachable connectors or other means. One example of a treatment procedure using first catheter 570 as part of the system shown in FIG. 5 begins by establishing an introducer sheath 580 in femoral vein 1005 through the thigh or groin area of patient 1000, which can be achieved using standard percutaneous access techniques. Although FIG. 5 illustrates introducer sheath 580 introduced into the right thigh or groin, insertion into the left thigh or groin area is also envisioned as well and may be preferable in some situations. A guidewire extends through introducer sheath 580, which can be an initial guidewire used for percutaneous access or a newly introduced guidewire. The guidewire can in certain forms have a diameter between 0.014 and 0.018 inches and a flexible distal tip that allows it to bend easily as it is advanced through the body to the selected site. The guidewire is maneuvered into common iliac vein 1010, through inferior vena cava 1015, and into right atrium 1020 of the heart 1025. The guidewire is then advanced into the coronary sinus (shown in more detail in FIG. 7) or other specific treatment area.

The distal end of first catheter 570 is advanced over the guidewire into femoral vein 1005, into common iliac vein 1010, inferior vena cava 1015 and into right atrium 1020. A hemostasis valve may also be present in first lumen port 565 as necessary to avoid significant loss of blood or other fluids during the catheter insertion process. In some embodiments of first catheter 570, a hemostatic device is built into first lumen port 565 and therefore no additional hemostasis valve over flow restrictor is required to avoid loss of blood.

When first catheter 570 is correctly positioned, the guidewire can be withdrawn from first lumen port 565 and first pressure sensing device 545 can be coupled to the proximal end of first catheter 570 by coupling a first lumen port 565 to first treatment outlet port 567. Second catheter 525 can then be inserted into first treatment inlet port 550 and guided through first pressure sensing device 545 and into the first lumen of first catheter 570 inside catheter shaft 575 until reaching the treatment region. Second catheter 525 is coupled to the treatment outlet port on second pressure sensing device 520 (not shown). Second treatment inlet port 512 is coupled to treatment line 510 which is in turn coupled to fluid input device 505 which is operable to deliver the treatment agent. First pressure sensing device 545 and second pressure sensing device 520 are activated and display first pressure data 555 and second pressure data 515 respectively.

With the pressure sensors, catheters, and treatment agent ready to be administered, balloon inflation device 535 can be employed to inflate the occlusion balloon at the distal end of first catheter 570 to hold catheter shaft 575 in place while also occluding the necessary portions of and/or adjacent to the target treatment region. Fluid input device 505 is operated to advance the treatment agent under pressure through a lumen of second catheter 525 to cause the treatment agent to flow into the treatment region. The increase in pressure within second catheter 525 due to the forceful passage of the treatment agent will appear as second pressure data 515 displayed by second pressure sensing device 520 and any corresponding changes in pressure within the in the treatment region will appear as first pressure data 555 displayed by first pressure sensing device 545. The operator can then monitor pressure data 515, 555 and adjust the pressure generated by fluid input device 505 accordingly, or make other necessary changes to optimize the therapy and/or avoid adverse effects to patient 1000 or to the treatment agent being administered.

While pressure monitoring in the target treatment region and in the treatment agent delivery lumen are identified and provided for in the preferred embodiments herein, it will be understood that pressure monitoring in other vascular locations during delivery of the therapeutic agent may also be undertaken. These include, for example, pressure measurement within congruent vessel structures, for example arterial-side pressure monitoring when applying venous-side retroperfusion or other delivery, or venous-side pressure monitoring in regions other than the target delivery region, e.g. for comparative purposes. These and other variations will be apparent to the person skilled in the field from the descriptions herein.

Figure 6:
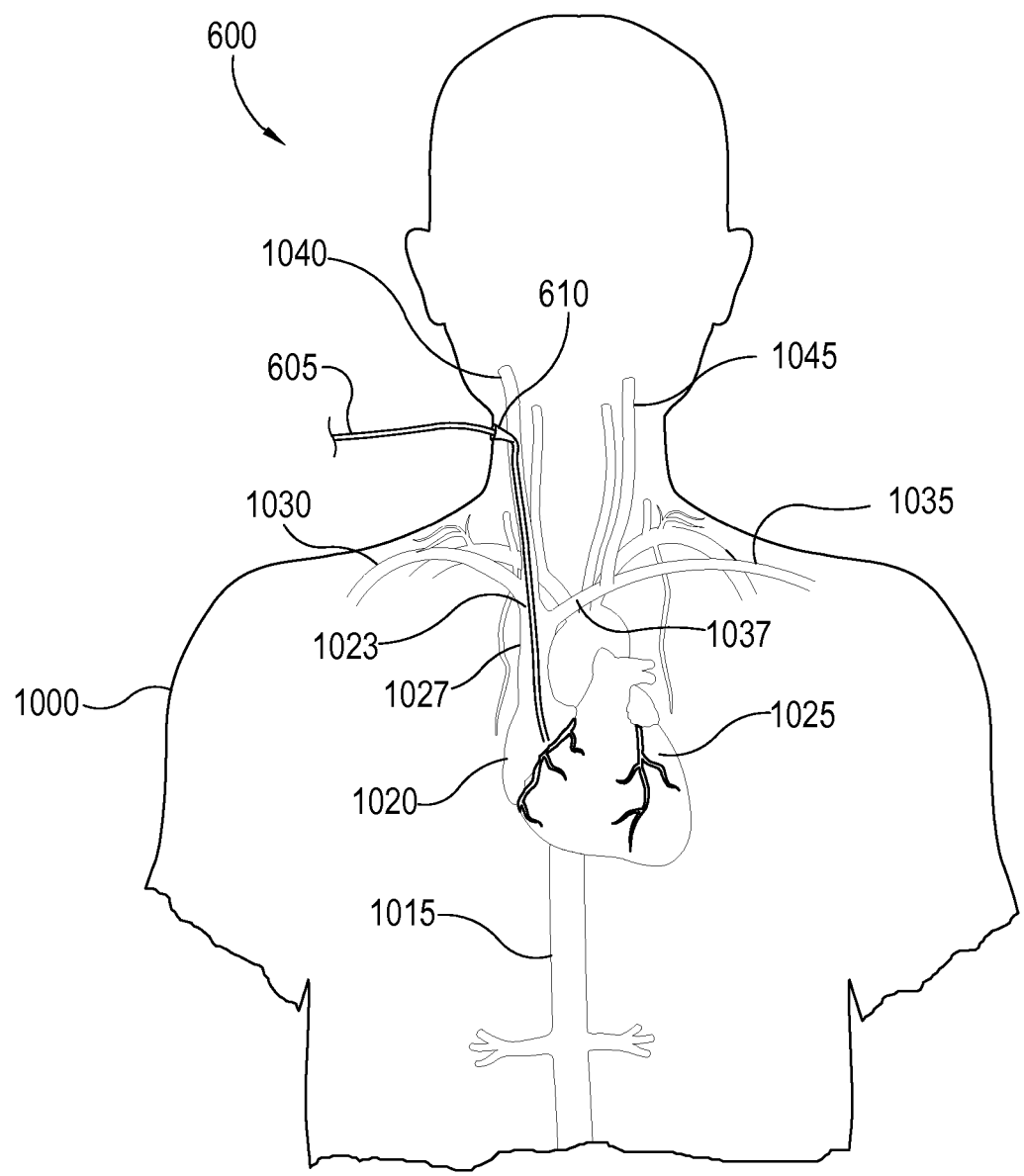
FIG. 6 is a diagram showing an alternate location for the insertion of the catheters shown in FIG. 3 and FIG. 5.

FIG. 3 and FIG. 5 illustrate the insertion of catheters in the groin or thigh area. FIG. 6 illustrates at 600 an alternate insertion point which may be preferable for some patients. An introducer sheath 610 is established percutaneously in the right internal jugular vein 1040 in the right side of the neck of patient 1000, instead of into a femoral vein as shown in FIG. 3 and FIG. 5. The procedure is continues as described above wherein a guidewire is extended through internal jugular vein 1040 and is maneuvered downward through the right innominate vein 1023, into superior vena cava 1027, and into right atrium 1020 of heart 1025 from above. Catheter shaft 605, which is similar to catheter shaft 380 shown in FIG. 3 and catheter shaft 575 shown in FIG. 5, is guided over the guidewire into right atrium 1020 of heart 1025. Equipment similar to that shown in FIG. 3 or FIG. 5 described above is then engaged as previously described to perform the treatment using the alternate insertion point. Other alternate insertion points are also envisioned. For example, introducer sheath 610 can also be established in left internal jugular vein 1045 in which case catheter shaft 605 is maneuvered through left internal jugular vein 1045 into left innominate vein 1035, into superior vena cava 1027 and right atrium 1020 of the heart 1025. Also, introducer sheath 610 may be established in left subclavian vein 1035 allowing catheter shaft 605 to pass through left subclavian vein 1035 and left innominate vein 1037 and into superior vena cava 1027 and into right atrium 1020. A similar positioning may be used but from the opposite side by inserting introducer sheath 610 into right subclavian vein 1030 in which case catheter shaft 605 can be maneuvered through right subclavian vein 1030 into right innominate vein 1023 and into the superior vena cava 1027 and right atrium 1020.

Figure 7:
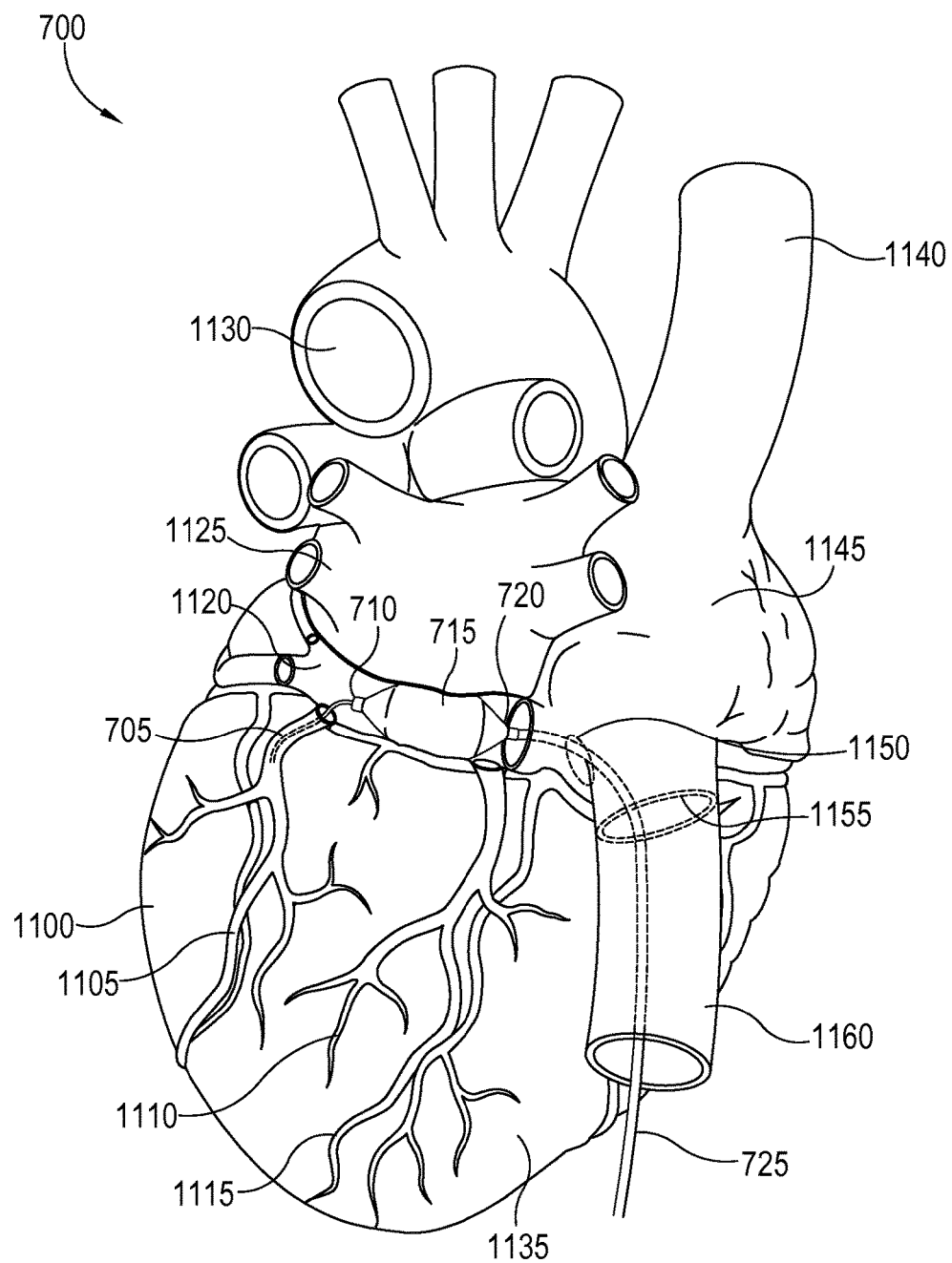
FIG. 7 shows the distal end of a catheter similar to the catheters illustrated in FIGS. 1-5 positioned within heart.

FIG. 7 illustrates at 700 one positioning of the distal end of a catheter system used for cell or other therapy of a type similar to the catheters illustrated in FIGS. 1-5 and described above. In FIG. 7, catheter 720 is positioned within the coronary sinus 1120 of the heart according to the techniques described above, or by other suitable technique. FIG. 7 shows a posterior view of the heart and illustrates several of the major blood vessels. The blood vessels, veins, arteries, and other major structures depicted in FIG. 7 are illustrative and are not necessarily anatomically correct in every detail regarding position, size, and relative scale. Several coronary veins 1105, 1110, and 1115, are illustrated and shown covering left ventricle 1100 and right ventricle 1135. These coronary veins branch off from coronary sinus 1120, a cutaway view of which is shown in FIG. 7. Above coronary sinus 1120 in FIG. 7 is left atrium 1125, and aorta 1130. Right atrium 1145 serves as the entry point for superior vena cava 1140, inferior vena cava 1160, and coronary sinus 1120. Superior vena cava 1140 delivers oxygen depleted blood from the upper half of the body while inferior vena cava 1160 delivers oxygen depleted blood from the lower half of the body. Coronary sinus 1120, provides a similar function with regard to the heart itself delivering oxygen depleted blood from the myocardial tissue to the right atrium through coronary sinus ostium 1150.

First catheter 720 is positioned generally in coronary sinus 1120 as illustrated in FIG. 7. Catheter shaft 725 enters right atrium 1145 through opening 1155 and turns to enter coronary sinus 1120 through coronary sinus ostium 1150. Catheter balloon 715 is adapted to occlude the coronary sinus or another vessel when inflated. In FIG. 7, catheter balloon 715 is positioned within coronary sinus 1120 and is inflated to partially or completely block the normal flow of oxygen depleted blood from the coronary sinus through coronary sinus ostium 1150 and into the right atrium. A second catheter 705 operating as a treatment delivery catheter is shown exiting distal tip 710 of first catheter 720 and entering coronary vein 1105. Second catheter 705 is positioned in this manner to deliver an appropriate treatment agent which may include fluids such as blood or blood components, various drugs, infusion pellets, suspended cells, stem cells, microspheres, peptide growth factors, DNA, RNA or other treatment agents, or any combination thereof. The treatment agent exiting second catheter 705 can be delivered into the myocardial tissue e.g. via the capillary beds in the treatment area opposite the normal circulation of blood from the coronary sinus 1120 into right atrium 1020 which is at least partially stopped by catheter balloon 715.

When present, a set curve in a distal portion of second catheter 705, e.g. as discussed in conjunction with catheters above, can facilitate steering the catheter 705 subselectively into various branches or regions of the local vasculature for delivery of the treatment agent.

FIG. 7 shows one possible positioning of second catheter 705, catheter balloon 715, and first catheter 720 for the introduction of an appropriate treatment agent. Depending on the desired outcome, the treatment agent used, and the procedure followed, catheter balloon 715 and first catheter 720 may be positioned deeper within coronary sinus 1120 or closer to coronary sinus ostium 1150, and/or within a coronary vein (e.g. an anterior descending coronary vein), thereby facilitating the positioning of second catheter 705 into other coronary veins such as 1110, 1115, or other veins not shown in FIG. 7. Likewise, the extent to which second catheter 705 extends beyond distal tip 710 of first catheter 720 is determined by the desired treatment as well. For example, it may be desirable to extend second catheter 705 further into coronary vein 1105, or into other coronary veins or vessels not shown in FIG. 7 to affect treatment in areas further removed from distal tip 710 and first catheter 720. One embodiment of second catheter 705 is similar to the catheter illustrated in FIG. 4 and described above which has a tip that has a set curve or bend from the longitudinal axis of second catheter 705 to aid in the process of traversing the tight corners and narrow passageways of the coronary veins branching out from coronary vein 1105, as discussed above.

Using the catheter illustrated in FIG. 7, other treatment options are also possible. For example, in a similar procedure, second catheter 705 is inserted deeper into a coronary vein such as coronary vein 1105, 1110, or 1115 and catheter balloon 715 is inflated to occlude coronary sinus 1120. As a treatment agent is infused from second catheter 705, second catheter 705 is simultaneously withdrawn gradually from coronary vein 1105 as the treatment agent is released into the myocardial tissue. As second catheter 705 passes the various branches of coronary vein 1105 during removal, second catheter 705 is advanced into these lesser branches of coronary vein 1105. The process is repeated whereby second catheter 705 is advanced into the lesser branch, and the treatment agent is delivered into these lesser branches of coronary vein 1105 as catheter 705 is then gradually withdrawn. This process allows for a more complete regional infiltration of the treatment agent into the myocardium in the treatment area.

Various techniques for guiding and positioning the catheter, guidewire, and catheter balloon illustrated in FIG. 1 through FIG. 7 are available depending on the goals of the treatment and the location of the treatment region. A common technique for aiding in catheter and guidewire positioning is to inject radiocontrast dyes into the bloodstream causing the blood vessels to be more easily visible under a fluoroscope. Another technique mentioned in the embodiments above that may be used in concert with radiocontrast dyes is to use a catheter having radiopaque markings or a catheter that is constructed with radiopaque filler material in the catheter shaft. These markings make the catheter or selected portions thereof visible under a fluoroscope as well. Once the blood vessels and catheter are both visible with the aid of fluoroscopy, the operator can use fluoroscopy to see, and manually control, the movements of the catheter in real-time as it is advanced through the patient's body and into the treatment region.

Recent techniques have been developed involving computers and advanced imaging techniques that significantly enhance the operator's ability to precisely navigate a catheter or guidewire into a treatment region. Any or all such techniques may be employed in treatment methods and systems described herein. In one example, an imaging technique such as computed tomography angiography, ultrasound or magnetic resonance imaging can be used to create a two-dimensional or three-dimensional map of the vasculature of a target region of a patient's heart. Such a map can be used in planning one or more target regions for receipt of the treatment agent. A catheter is then inserted percutaneously and guided into the treatment area through a coronary vein or artery, while imaging the movement of the catheter in real time, for example using at least a distal tip fluoroscopic marker (e.g. radiopaque markers 485 in the Figs. herein) or other suitable imaging marker. This real time image is overlaid upon the map as the procedure is conducted to facilitate effective application of the therapy by a user referencing the real-time image and map. Such an arrangement may improve accuracy, reduce the chance of misdirection into the wrong vessel or damage to the vessels themselves, and allows for precision positioning of the catheter and administration of the treatment agent.

As to the treatment or therapeutic agent administered, in certain embodiments, any one or combination of a wide variety of cellular preparations may administered to a patient using a device, system or method described herein. For example, the cells can be skin cells, skeletal muscle cells, cardiac muscle cells, lung cells, mesentery cells, or adipose cells. The adipose cells may be from omental fat, properitoneal fat, perirenal fat, pericardial fat, subcutaneous fat, breast fat, or epididymal fat. In certain embodiments, the cells comprise stromal cells, stem cells, or combinations thereof. As used herein, the term "stem cells" is used in a broad sense and includes traditional stem cells, adipose derived stem cells, progenitor cells, preprogenitor cells, reserve cells, and the like. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Additional illustrative cells which can be used include hepatocytes, epithelial cells, Kupffer cells, fibroblasts, neurons, cardiomyocytes, myocytes, chondrocytes, pancreatic acinar cells, islets of Langerhans, osteocytes, myoblasts, satellite cells, endothelial cells, adipocytes, preadipocytes, biliary epithelial cells, and progentior cells of any of these cell types.

In some embodiments, the cells are, or include, endothelial progenitor cells (EPCs). Preferred EPCs for use in the invention are endothelial colony forming cells (ECFCs), especially ECFCs with high proliferative potential. Suitable such cells are described for example in U.S. Patent Application Publication No. 20050266556 published Dec. 1, 2005, publishing U.S. patent application Ser. No. 11/055, 182 filed Feb. 9, 2005, and U.S. Patent Application Publication No. 20080025956 published Jan. 1, 2008, publishing U.S. patent application Ser. No. 11/837,999, filed Aug. 13, 2007, each of which is hereby incorporated by reference in its entirety. Such ECFC cells can be a clonal population, and/or can be obtained from umbilical cord blood of humans or other animals. Additionally or alternatively, the endothelial colony forming cells have the following characteristics: (a) express the cell surface antigens CD31, CD105, CD146, and CD144; and/or (b) do not express CD45 and CD 14; and/or (c) ingest acetylated LDL; and/or (d) replate into at least secondary colonies of at least 2000 cells when plated from a single cell; and/or (e) express high levels of telomerase, at least 34% of that expressed by HeLa cells; and/or (f) exhibit a nuclear to cytoplasmic ratio that is greater than 0.8; and/or (g) have cell diameters of less than about 22 microns. Any combination of some or all of these features (a)-(g) may characterize ECFCs used in the present invention.

In other embodiments, the cells are, or include, muscle derived cells, including muscle derived myoblasts and/or muscle derived stem cells. Suitable such stem cells and methods for obtaining them are described, for example, in U.S. Pat. No. 6,866,842 and U.S. Pat. No. 7,155,417, each of which is hereby incorporated herein by reference in its entirety. The muscle derived cells can express desmin, M-cadherin, MyoD, myogenin, CD34, and/or Bcl-2, and can lack expression of CD45 or c-Kit cell markers.

In still other embodiments, the cells are, or include, stem cells derived from adipose tissue. Suitable such cells and methods for obtaining them are described for example in U.S. Pat. No. 6,777,231 and U.S. Pat. No. 7,595,043, each of which is hereby incorporated herein by reference in its entirety. The cellular population can include adipose-derived stem and regenerative cells, sometimes also referred to as stromal vascular fraction cells, which can be a mixed population including stem cells, endothelial progenitor cells, leukocytes, endothelial cells, and vascular smooth muscle cells, which can be adult-derived. In certain forms, the cellular preparation can include adipose-derived cells that can differentiate into two or more of a bone cell, a cartilage cell, a nerve cell, or a muscle cell.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. An apparatus, comprising:
   a catheter shaft defining a first lumen and a second lumen;
   a proximal port in fluid communication with the first lumen, the proximal port having associated therewith a resilient valve member operable to seal around an infusion catheter extended through the proximal port;
   a first sensor, the first sensor operable to measure fluid pressure in the first lumen;
   a distal port in fluid communication with the first lumen, the distal port positionable within a vascular vessel of a patient and arranged to receive blood under pressure when positioned in the vascular vessel;
   an inflatable balloon mounted on the catheter shaft proximal of the distal port, the inflatable balloon having an inner void in fluid communication with the second lumen;
   the infusion catheter coaxially received within the first lumen, the infusion catheter having an infusion catheter shaft and a proximal port in fluid communication with an infusion lumen;
   a liquid input device in fluid communication with the proximal port of the infusion catheter;
   a second sensor, the second sensor associated with the infusion lumen and operable to measure pressure of fluid forced into the proximal port of the infusion catheter by the liquid input device; and
   a proximal inflation port in fluid communication with the second lumen;
   wherein the second sensor is disposed between the liquid input device and the infusion catheter; and
   wherein the liquid input device is removably coupled to the second sensor.

2. The apparatus of claim 1, wherein the first sensor is positioned to sense fluid pressure from a location within the first lumen.

3. The apparatus of claim 1, wherein the first sensor is operable to measure fluid pressure in the first lumen indicative of a fluid pressure occurring at said distal port.

4. The apparatus of claim 1, wherein the first sensor is mounted on a hub member defining the proximal port and a proximal inflation port of the catheter shaft.

5. The apparatus of claim 1, wherein:
   the infusion catheter is received coaxially through the first lumen in rotatable fashion, the infusion catheter including a distal tip region having a set curved condition offset at an angle from about 3 to about 90 degrees from a longitudinal axis of the infusion catheter shaft.

6. The apparatus of claim 5, wherein said catheter shaft defining said first lumen also has a distal tip region having a set curved condition.

7. The apparatus of claim 6, wherein the distal tip region of the catheter shaft defining said first lumen is offset at an angle from about 3 to about 90 degrees from a longitudinal axis of the catheter shaft.

8. The apparatus of claim 5, wherein the infusion catheter shaft comprises a metal braid terminating proximal of the distal tip region of the infusion catheter, and wherein the infusion catheter includes a distal tip radiopaque marker.

9. The apparatus of claim 5, wherein the infusion catheter also includes an inflatable balloon mounted on the infusion catheter shaft.

10. The apparatus of claim 5, also including a guidewire receivable through the lumen of the infusion catheter.

11. The apparatus of claim 1, wherein the infusion catheter includes:
   an inflatable balloon mounted on a distal portion of the infusion catheter shaft;
   an inflation lumen extending through the infusion catheter shaft, for inflating the inflatable balloon;
   at least one port in a distal region of the infusion catheter shaft occurring distally of the inflatable balloon, the infusion lumen extending through the infusion catheter shaft to the at least one port; and
   at least one of:

(a) an ultrasound emitting element mounted on the distal region of the infusion catheter shaft;
(b) a set curve in the distal region of the infusion catheter shaft; and
(c) said at least one port including a plurality of sidewall ports in fluid communication with the infusion lumen;
wherein the infusion catheter shaft has an outer diameter of about 1 mm or less.

12. The apparatus of claim 11, including both (a) an ultrasound emitting element mounted on the distal region of the infusion catheter shaft, and (b) a set curve in the distal region of the infusion catheter shaft.

13. The apparatus of claim 11, including both (a) an ultrasound emitting element mounted on the distal region of the infusion catheter shaft, and (c) said at least one port including a plurality of sidewall ports in fluid communication with the infusion lumen.

14. The apparatus of claim 11, including both (b) a set curve in the distal region of the infusion catheter shaft, and (c) said at least one port including a plurality of sidewall ports in fluid communication with the infusion lumen.

15. The apparatus of claim 1, wherein the second sensor is removably coupled to the infusion catheter.

16. The apparatus of claim 1, wherein the first sensor is removably coupled to the catheter shaft.

17. The apparatus of claim 1, wherein the first sensor is positioned at a distal tip of the catheter shaft.

18. A system useful for infusion of liquid medium under pressure, comprising:
a first catheter having a first catheter shaft defining a first lumen and an inflation lumen, the first lumen communicating with a first lumen proximal port and a first lumen distal port, the first catheter including an inflatable balloon mounted on the first catheter shaft and the inflation lumen defined by the first catheter shaft and extending from a proximal inflation port to a distal port in fluid communication with an inner void of the inflatable balloon;
a first sensor, the first sensor operable to measure fluid pressure generated in the first lumen when the first lumen distal port is positioned in a vascular vessel of a patient;
a second catheter having a second catheter shaft defining a second catheter lumen, the second catheter shaft receivable coaxially through the first lumen of the first catheter; and
a second sensor, the second sensor operable to measure pressure of liquid forced into the second catheter lumen; and
a liquid input device fluidly communicating with the second catheter lumen and operable to force liquid under pressure into the second catheter lumen;
wherein the second sensor is disposed between the liquid input device and the second catheter; and
wherein the liquid input device is removably coupled to the second sensor.

19. The system of claim 18, wherein the second sensor is positioned between the liquid input device and the second catheter lumen.

20. The system of claim 18, wherein the second catheter includes an inflatable balloon mounted on the second catheter shaft.

21. The system of claim 18, wherein one or both of the first catheter and second catheter includes a distal portion having a set curved condition.

22. The system of claim 18, wherein the second sensor is removably coupled to the second catheter.

23. The system of claim 18, wherein the first sensor is removably coupled to the first catheter.

24. The system of claim 18, wherein the first sensor is mounted on a hub member defining the first lumen proximal port and the proximal inflation port of the first catheter so as to sense fluid pressure within the first lumen.

25. The system of claim 18, wherein the first sensor is positioned at a distal tip of the first catheter.

* * * * *